United States Patent [19]
Green et al.

[11] 4,222,416
[45] Sep. 16, 1980

[54] APPARATUS FOR CONTROLLABLY DISPENSING A VISCOUS RESIN AND REACTIVE HARDENER

[75] Inventors: William Green, Irvington; Sidney Heisler, Colonia; Jay Riazanow, Rockaway, all of N.J.

[73] Assignee: Oxydental Products, Inc., Irvington, N.J.

[21] Appl. No.: 959,869

[22] Filed: Nov. 13, 1978

[51] Int. Cl.² ............................................. B65B 3/04
[52] U.S. Cl. ................................... 141/27; 141/82; 141/284; 222/129; 222/165; 366/24
[58] Field of Search ..................... 141/1–12, 141/18–27, 100, 104, 105, 106, 250–284, 369–381, 82; 222/165, 166, 129; 221/150 R, 150 A, 200; 366/24

[56] References Cited
U.S. PATENT DOCUMENTS
1,557,273  10/1925  Secrist .................................. 222/165

Primary Examiner—Houston S. Bell, Jr.
Attorney, Agent, or Firm—Eugene Lieberstein

[57] ABSTRACT

The apparatus comprises a housing having individual compartments for separately storing an epoxy resin material and a reactive hardener for the epoxy resin, a rotatably adjustable housing having a first and second stationary position, an aperture for each compartment disposed in the first position above the level of each material and disposed in the second position below the level of each material and a syringe for each aperture for extracting and dispensing a predetermined measure of each material.

9 Claims, 4 Drawing Figures

APPARATUS FOR CONTROLLABLY DISPENSING A VISCOUS RESIN AND REACTIVE HARDENER

This invention relates to liquid dispensing apparatus and more particularly to apparatus for dispensing a liquid epoxy resin and a reactive hardener in a predetermined proportion relative to one another.

In the practice of prosthetic dentistry, inlays, crowns and fixed partial dentures are indirectly made by forming a casting on a die. One conventional die material is an epoxy resin which is polymerized into a solid in the presence of a curing agent hereinafter referred to as a reactive hardener. The composition of the epoxy resin die material is selected for its cured physical properties such as strength, abrasion resistance, dimensional stability etc., as well as for its handling characteristics and clinical performance.

All conventional liquid epoxy resins are highly viscous and retain their fluid characteristics until cured. Once cured into a solid the procedure is irreversible. Accordingly, the epoxy resin and reactive hardener must be kept apart until combined in the preparation of the mold. To assure a proper consistency a predetermined measure of each must be added together. Currently available equipment, used in a dental laboratory or doctor's office, for automatically dispensing epoxy resin and reactive hardener in a predetermined proportion, requires extensive servicing due to clogging and breakdown. In addition, commercially available dispensing equipment is expensive as well as operationally cumbersome and unwieldy.

The apparatus of the present invention is relatively inexpensive and permits the dispensing of a measured quantity of a predetermined epoxy resin material and reactive hardener in a simple reliable manner requiring no operational skill and little maintenance.

The apparatus of the present invention comprises, in combination; a housing having separate compartments for individually storing an epoxy resin material and a liquid reactive hardener respectively, means for rotationally mounting the housing about a longitudinal axis, stop means for holding the housing stationary in either a predetermined first or second position, an aperture for each compartment within said housing, with each aperture extending through the housing on a common face thereof and in a predetermined location such that in the first stationary position each aperture lies above the surface level of said epoxy resin and reactive hardener respectively and in the second stationary position each aperture lies below the surface level of said epoxy resin and reactive hardener and syringe means extending into each compartment through each aperture with the syringe means adapted in the second stationary position to withdraw a predetermined measure of said epoxy resin and reactive hardener and for separately dispensing each in a predetermined position.

It is therefore the principal object of the present invention to provide dispensing apparatus for an epoxy resin material and a reactive hardener.

It is another object of the present invention to provide dispensing apparatus for an epoxy resin material and a reactive hardener in which each material is dispensed separately in a predetermined proportion relative to each other.

Other objects and advantages of the present invention will become apparent from the following detailed description thereof when read in conjunction with the accompanying drawings in which.

Figure 1:
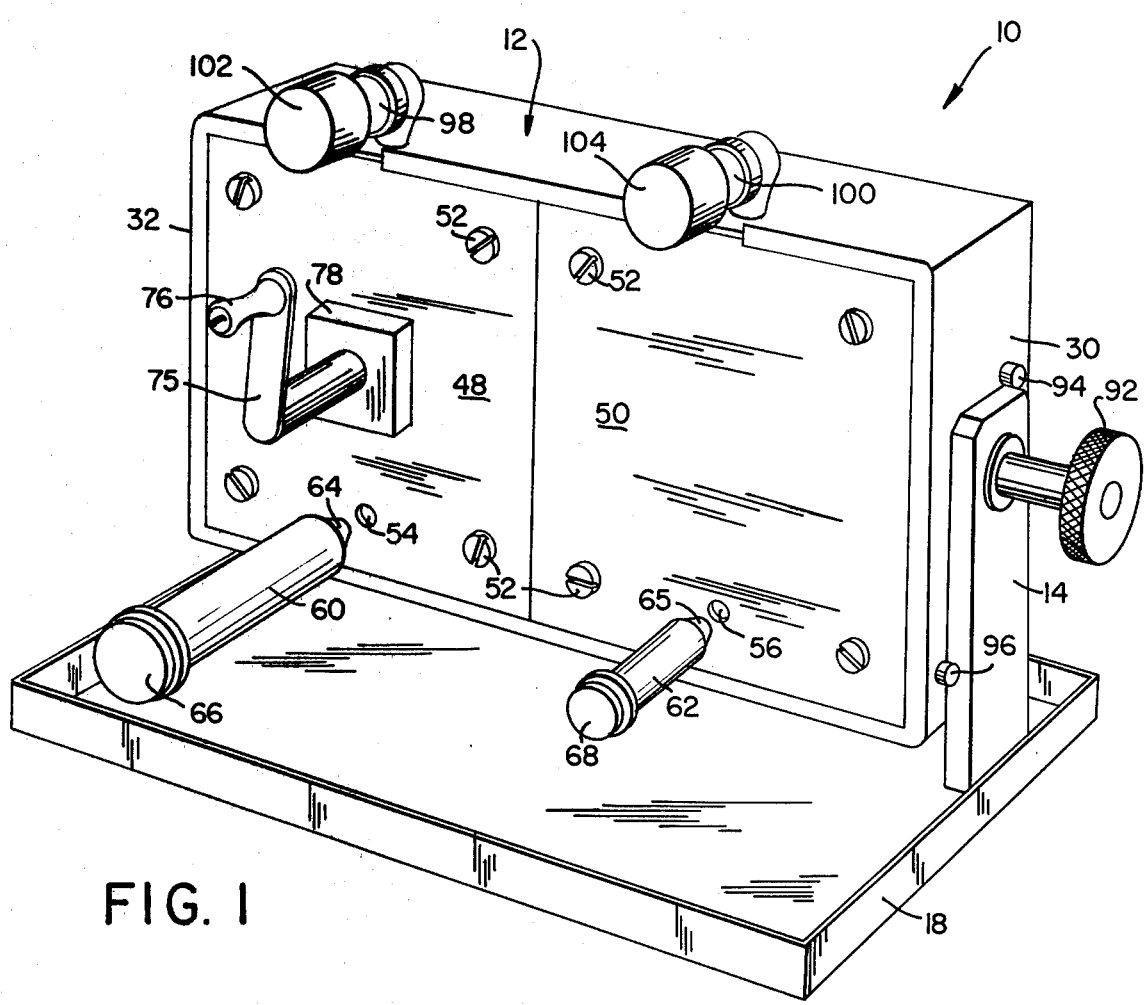
FIG. 1 is a perspective view of the dispensing apparatus of the present invention in the stationary position for withdrawal of a predetermined measure of the epoxy resin material and reactive hardener respectively.
Figure 2:
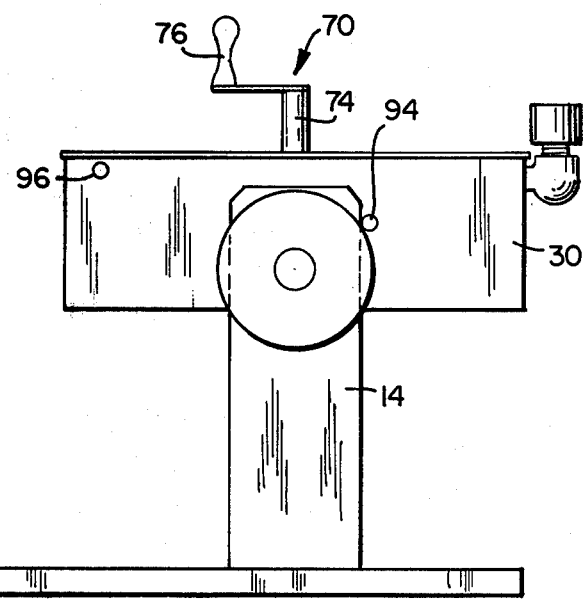
FIG. 2 is an end view of the assembly of FIG. 1 in another stationary position for filling the compartments in the apparatus of FIG. 1 with the epoxy resin material and reactive hardener.
Figure 3:
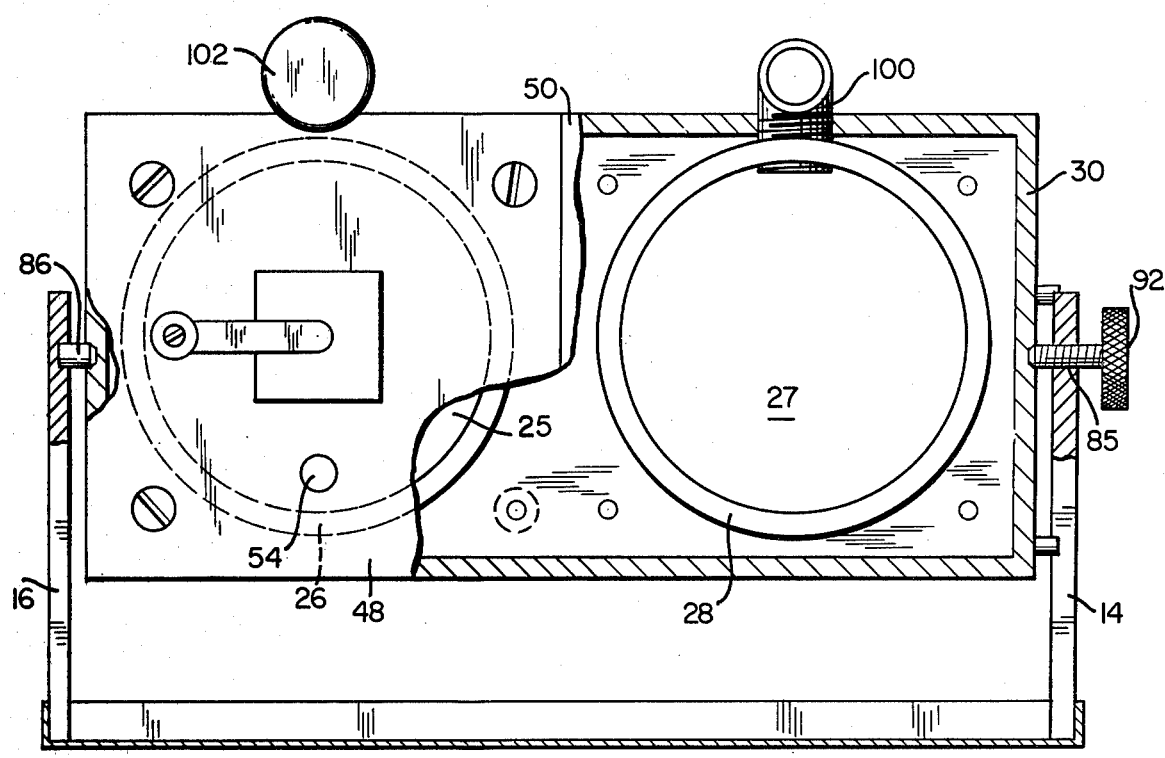
FIG. 3 is a front elevation partly in section of the apparatus of FIG. 1.
Figure 4:
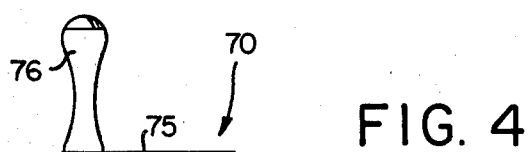
FIG. 4 is another sectional view of the apparatus of the present invention taken along the lines 4—4 of FIG. 2.

The same reference numerals are used throughout the several views of the present invention to identify the same components. The dispensing apparatus 10 as shown in FIGS. 1-4 inclusive comprises a housing 12 supported upon a pair of brackets 14 and 16 which extend vertically from a base pan 18. The brackets and base pan form a frame between which the housing is suspended in a manner which permits the housing 12 to be manually rotated about a longitudinal axis into one of two stationary positions as will be discussed in more detail hereafter.

The housing 12 is of a generally rectangular configuration preferably of metal with a hollow interior 20 into which two containers 22 and 24 are placed. The containers 22 and 24 represent separate compartments for storing two viscous liquids such as an epoxy resin and reactive hardener with each being of any conventional composition. The containers 22 and 24 are preferably cylindrical in geometry. Each container has an open end 25 and 27 respectively and an outer rim 26 and 28 circumferentially extending from each open end thereof. The side walls 30 and 32 of the housing 12 each have a recess 34 and 36 which forms a ledge for supporting a plate 38. The plate 38 is held in position affixed to the side walls 30 and 32 of the housing 12 by screws 40 and 42.

The containers 22 and 24 are passed through openings formed in the plate 38 with each rim 26 and 28 resting over the edge of each opening for suspending the containers within the housing 12. A gasket or "O" ring 44 and 46 is placed over each rim 26 and 28 before covering each container with a cover plate 48 and 50. The "O" rings prevent leakage of the fluid contents from the containers when the housing is rotatably adjusted into an upright position as will become apparent hereafter. The cover plates 48 and 50 are secured to the plate 38 through mounting screws 52.

A dispensing aperture 54 and 56 is formed in each cover plate 48 and 50 in a predetermined location adjoining the open top 25 and 27 of each container 22 and 24 such that the liquid contents in each container can be extracted therefrom when the housing is rotatably adjusted into an upright position as will be explained in more detail hereafter. Each dispensing aperture 54 and 56 should be positioned relative to the open top of each container 22 and 24 to permit complete withdrawal of the stored materials. The dispensing apertures 54 and 56 provide the only access into the containers 22 and 24 from outside the housing 12 for dispensing the epoxy resin and hardener. For an epoxy resin and reactive hardener combination it is preferable for the container storing the epoxy resin, e.g., the container 22 to have a dispensing aperture somewhat larger in diameter than the corresponding dispensing aperture 56 communicating with the open top of the container storing the reactive hardener, i.e., container 24.

A pair of hypodermic syringe filling devices 60 and 62 pass through the dispensing apertures 54 and 56 into the respective containers 22 and 24. Although any type of conventional hypodermic syringe may be used the type of syringe preferred is one having a generally conical funnel shaped front end 64 and 65 respectively. The diameter of the dispensing aperture will determine the appropriate size of syringe needed. The front end of each syringe will upon entry into the corresponding dispensing aperture 54 and 56 operate to effectively seal each aperture from leakage. The syringes 60 and 62 function in a conventional manner requiring an operator to pull the plunger 66, 68 of each syringe in order to extract a predetermined measure of liquid material from the containers 22 and 24 respectively. The syringe 60 is larger than the syringe 62 to automatically accommodate for the different ratio of epoxy resin to reactive hardener material as required for the preparation of the die. Alternatively each dispensing aperture and syringe may be of the same size in which case the operator would have to be more careful in extracting the proper amount of material from each compartment.

The housing 12 is suspended for rotation between its opposite ends by axle members 84 and 86 which extend from the support brackets 14 and 16 and co-fit within chamfered recesses 88 and 90 in the side walls 30 and 32 of the housing 12. A set screw is preferably used for the axle member 84 which threadably engages the bracket 14 through a threaded opening 85. A knurled knob 92 is connected to one end of the axle member 84 for manually tightening or loosening the engagement of the axle member 84 against the housing 12. The other axle member 86 extends from bracket 16 and need not be laterally adjustable. A pair of stop arms 94 and 96 longitudinally extend from the side wall 30 of the housing 12 to limit the disposition of the housing 12 to two predetermined stationary positions. The stop arms 94 and 96 are positioned relative to one another to limit the rotation of the housing 12 between the two stationary positions through an angle of preferably about ninety degrees. The first position is established when the stop arm 94 engages bracket 14 and the second position when the stop arm 96 engages bracket 14. The stop arms 94 and 96 may have any geometry and can be secured to the side wall 30 in any conventional manner.

The housing 12 includes a manually operated mixer 70 having a paddle 72 disposed within the container 22 to permit stirring of the viscous epoxy resin through rotation of the handle 76. An arm 74 extends through a bore in the cover plate 48 to connect the paddle 72 to the handle 76 through a link 75. The mixer 70 is supported by a mounting block 78 connected to the cover plate 48. The mounting block 78 includes a bushing (not shown) for rotationally supporting the arm 74.

The housing also includes a conventional heating pad 80 surrounding the container 22. The heating pad 80 is electrically connected to wire conduit 81 which passes through the housing 12 at opening 82 for connection to a standard electrical outlet.

A pair of threaded pipe conduits 98 and 100 extend through the housing 12 into the containers 22 and 24 to permit them to be filled with an epoxy resin and reactive hardener respectively. A terminal cap 102 and 104 is used to cover the pipe conduits 98 and 100 after filling the containers 22 and 24.

In operation, the containers 22 and 24 are filled through the pipe conduits 98 and 100 which are then closed using the terminal caps 102 and 104. The filling operation should occur with the housing 12 in a prone position, i.e., with the stop arm 94 engaging the bracket 14. In such position the dispensing apertures 54 and 56 lie above the surface level of both the epoxy resin stored in container 22 and the reactive hardener stored in container 24. While in this position the syringe filling devices 60 and 62 are inserted into the appropriate dispensing apertures 54 and 56 and should remain therein until the materials are to be dispensed.

To dispense a measured quantity of epoxy resin and reactive hardener the housing 12 is first rotated from a stationary prone position into a stationary upright position with stop arm 96 engaging the bracket 14. In the upright position the plungers 66 and 68 of the syringe devices are pulled back to extract the desired proportions of fluid from each container. The housing is then rotated back into the prone position for withdrawing the syringes and dispensing the liquids.

For highly viscous epoxy resin compositions it is preferred to heat the composition by means of the heating pad 80 and in addition, to stir the composition prior to extraction.

What is claimed is:

1. Apparatus for separately dispensing a viscous epoxy resin material and a liquid material hardener for said epoxy resin in a measured proportion to one another comprising, in combination:
   a housing including at least two compartments with each containing one of said materials;
   means for adjustably rotating said housing about a longitudinal axis between a first and second stationary position;
   a first aperture communication with said compartment storing said epoxy resin material;
   a second aperture communicating with said compartment storing said liquid material hardener;
   said first and second apertures being exposed to the exterior of said housing with each being in a predetermined location such that in said first stationary position each aperture lies above the surface level of each material and in said second stationary position each aperture lies below the surface level of each material; and
   first and second syringe means extending into each compartment through each aperture for separately withdrawing and dispensing a predetermined measure of said epoxy resin and reactive hardener in a predetermined proportion.

2. Apparatus as defined in claim 1 wherein said first aperture is of a diameter larger in size than the diameter of said second aperture and wherein said first and second syringe means is of a size corresponding to the counterpart size of said first and second apertures.

3. Apparatus as defined in claim 2 wherein each syringe means has a conical shaped end adapted to secure each aperture from leakage.

4. Apparatus as defined in claims 1 or 3 wherein said means for adjustably rotating said housing comprises a frame having two vertically disposed ends and means for rotationally suspending said housing from said two ends.

5. Apparatus as defined in claim 4 further comprising first and second stop means extending from said housing and arranged relative to one another to engage an end of said frame during rotation of said housing for establishing said first and second stationary position respectively.

6. Apparatus as defined in claim 5 wherein said first and second stop means are disposed relative to one another to limit rotation of the housing to an angle of about ninety degrees.

7. Apparatus as defined in claim 6 wherein said housing is a rectangular construction and wherein each compartment is formed from a removable container.

8. Apparatus as defined in claim 6 further comprising means for mixing the epoxy resin within said housing.

9. Apparatus as defined in claim 8 further comprising a heating pad surrounding said compartment storing said epoxy resin.

* * * * *